United States Patent
Zhang et al.

(10) Patent No.: US 8,755,869 B2
(45) Date of Patent: Jun. 17, 2014

(54) ADJUSTING NEIGHBORHOOD WIDTHS OF CANDIDATE HEART BEATS ACCORDING TO PREVIOUS HEART BEAT STATISTICS

(75) Inventors: Jicong Zhang, Gainesville, FL (US); Wangcai Liao, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 118 days.

(21) Appl. No.: 13/098,023

(22) Filed: Apr. 29, 2011

(65) Prior Publication Data
US 2012/0277816 A1 Nov. 1, 2012

(51) Int. Cl.
*A61B 5/04* (2006.01)
(52) U.S. Cl.
USPC .................................................. 600/509
(58) Field of Classification Search
USPC .................. 600/508–509, 515–516
See application file for complete search history.

(56) References Cited

U.S. PATENT DOCUMENTS

| | | | |
|---|---|---|---|
| 2006/0041201 A1* | 2/2006 | Behbehani et al. | 600/521 |
| 2006/0281998 A1* | 12/2006 | Li | 600/516 |
| 2008/0319281 A1* | 12/2008 | Aarts | 600/301 |
| 2009/0043216 A1* | 2/2009 | Lin et al. | 600/501 |

FOREIGN PATENT DOCUMENTS

WO 2007043903 A1 4/2007

OTHER PUBLICATIONS

International Application No. PCT/US2012/031370, Search Report and Written Opinion dated Jun. 19, 2012, 14 pages.

* cited by examiner

*Primary Examiner* — Rex R Holmes
(74) *Attorney, Agent, or Firm* — Cyberonics, Inc.

(57) ABSTRACT

Methods and systems for adjusting neighborhood widths of candidate heart beats, including being provided with a plurality of candidate heart beats, the candidate heart beats being associated with neighborhood widths in the time domain, and scaling the neighborhood widths, an amount of scaling being determined according to one or more previous heart rate statistics.

21 Claims, 9 Drawing Sheets

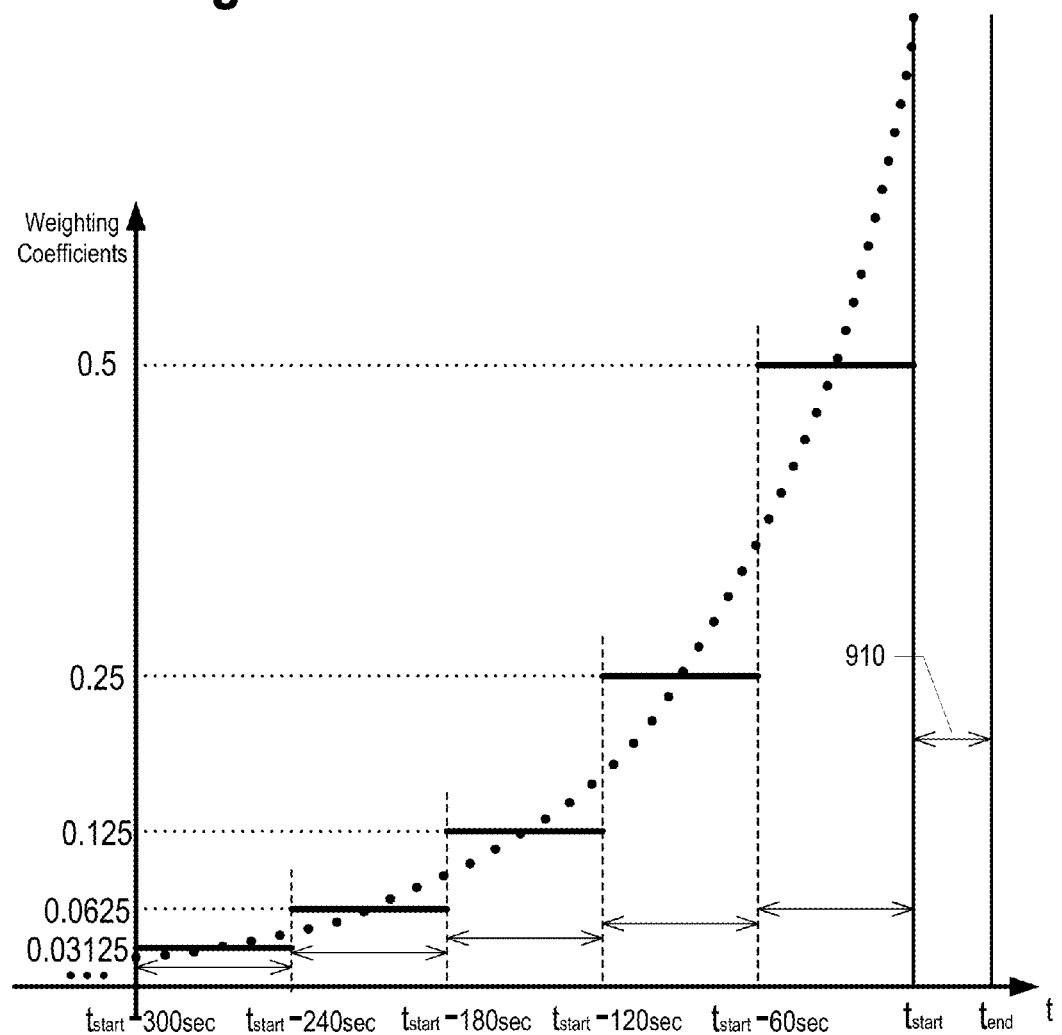

ADJUSTING NEIGHBORHOOD WIDTHS OF CANDIDATE HEART BEATS ACCORDING TO PREVIOUS HEART BEAT STATISTICS

A. BACKGROUND

1. Technical Field of the Present Disclosure

The present disclosure relates generally to the field of adjusting the neighborhood widths of detected candidate heart beats of a subject according to the subject's recent and/or historical heart rate statistics.

2. Background of the Present Disclosure

Reliable detection of a subject's heart beat is important in determining the subject's heart rate, which may be used to assess the subject's medical condition. Typically, an electrocardiogram (ECG) may be used to detect the R-wave portion of the heart's electrical signals. Various noise and artifacts may be present in ECG signals, however. The noise and muscle artifacts may be much stronger or substantially equal to the ECG signal in amplitude and may also overlap with the ECG signal in the frequency domain in some surface ECG applications, for example. Accordingly, the presence of the noise and artifacts can make it more difficult to differentiate true R-waves from false R-waves.

B. SUMMARY

In one respect, disclosed is a method for adjusting neighborhood widths of candidate heart beats, the method comprising being provided with a plurality of candidate heart beats, the candidate heart beats being associated with neighborhood widths in the time domain, and scaling the neighborhood widths, an amount of scaling being determined according to one or more previous heart rate statistics.

In another respect, disclosed is a system for adjusting neighborhood widths of candidate heart beats, the system comprising one or more processors, one or more memory units coupled to the one or more processors, the system being configured to be provided with a plurality of candidate heart beats, the candidate heart beats being associated with neighborhood widths in the time domain, and scale the neighborhood widths, an amount of scaling being determined according to one or more previous heart rate statistics.

In yet another respect, disclosed is a computer program product embodied in a computer-operable medium, the computer program product comprising logic instructions, the logic instructions being effective to be provided with a plurality of candidate heart beats, the candidate heart beats being associated with neighborhood widths in the time domain, and scale the neighborhood widths, an amount of scaling being determined according to one or more previous heart rate statistics.

Numerous additional embodiments are also possible.

C. BRIEF DESCRIPTION OF THE DRAWINGS

Other objects and advantages of the present disclosure may become apparent upon reading the detailed description and upon reference to the accompanying drawings.

FIG. 9 is a graphical diagram illustrating an example of previous heart rate statistics where exponentially decreasing weights are used with the previous heart rate data, in accordance with some embodiments.

Figure 1:
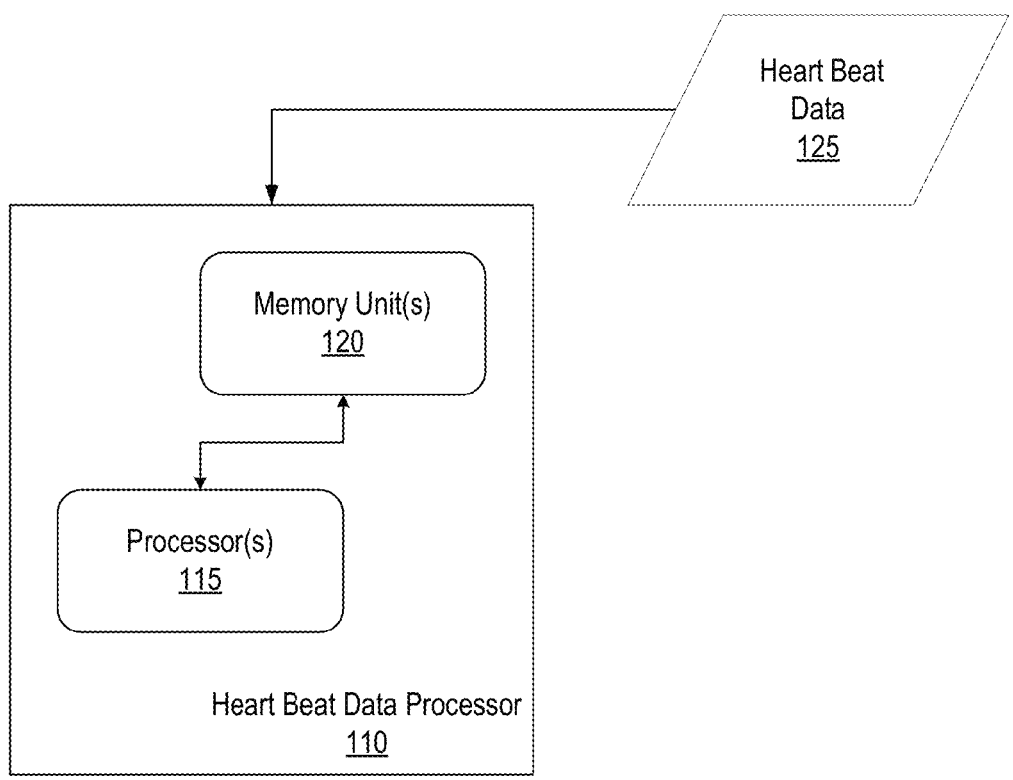
FIG. 1 is a block diagram illustrating a system for adjusting neighborhood widths of candidate heart beats according to a previous heart rate statistics, in accordance with some embodiments.

While the present disclosure is subject to various modifications and alternative forms, specific embodiments of the claimed subject matter are shown by way of example in the drawings and the accompanying detailed description. The drawings and detailed description are not intended to limit the present claimed subject matter to the particular embodiments. This disclosure is instead intended to cover all modifications, equivalents, and alternatives falling within the scope of the present claimed subject matter.

D. DETAILED DESCRIPTION

One or more embodiments of the present claimed subject matter are described below. It should be noted that these and any other embodiments are exemplary and are intended to be illustrative of the claimed subject matter rather than limiting. While the present claimed subject matter is widely applicable to different types of systems, it is impossible to include all of the possible embodiments and contexts of the present claimed subject matter in this disclosure. Upon reading this disclosure, many alternative embodiments of the present claimed subject matter will be apparent to persons of ordinary skill in the art.

The various illustrative logical blocks, modules, circuits, and algorithm steps described in connection with the embodiments disclosed here may be implemented as electronic/computer hardware, computer software, or combinations of the two. Various illustrative components, blocks, modules, circuits, and steps are described generally in terms of their functionality. Whether such functionality is implemented as hardware or software may depend upon the particular application and imposed design constraints. The described functionality may be implemented in varying ways for each particular application, but such implementation decisions should not be interpreted as causing a departure from the scope of the present claimed subject matter.

In some embodiments, systems and methods are disclosed for adjusting neighborhood widths of candidate heart beats in a time window from a subject. A sequence of candidate heart beats (with associated time stamps) may be received and/or detected. The candidate heart beats may be detected from real time ECG recordings or near real time or the candidate heart beats may be received from previously recorded ECG recordings or heart beat data.

FIG. 1 is a block diagram illustrating a system for adjusting neighborhood widths of candidate heart beats according to a previous heart rate statistics, in accordance with some embodiments.

In some embodiments, heart beat data processor 110 is configured to receive and analyze heart beat data 125 as described here. Heart beat data 125 may be raw ECG recordings or filtered or preprocessed ECG recordings at given points in time (generally in a given time window). The heart beat data may be received in real time or near real time from a subject, or the heart beat data may be previously recorded and is being received from a storage device.

In some embodiments, heart beat data processor 110 is configured to filter and preprocess ECG data, calculate multiple features, generate candidate heart beats, calculate corresponding individualized likelihood scores, and analyze the data and identify which of the candidate heart beats/R-waves are true and which are false. Heart beat data processor 110 may be configured, in some embodiments, to calculate a likelihood score for each candidate, to calculate a corresponding neighborhood width for each candidate, and to apply a scaling to the neighborhood widths of candidate R-waves within a time window according to previous heart rate statistics of a subject.

The functionality of heart beat data processor 110 may be implemented using one or more processors such as processor(s) 115 and one or more memory units coupled to the one or more processors such as memory unit(s) 120.

In some embodiments, conditioning and other types of filtering (such as wavelet transform, band pass filtering, differential value calculation) may be applied to the candidate heart beats prior to additional heart beat processing.

In some embodiments, a neighborhood width in the time domain may be assigned to the candidate heart beats, where the neighborhood width may indicate an extent in the time domain of each of the candidate heart beats. The neighborhood widths may be accordingly used in the selection of true heart beats from the candidate heart beats. In some embodiments, a condition may be imposed, for example, that the neighborhoods of two or more true heart beats may not overlap. That is, if two or more neighborhood widths overlap, only one of those candidate heart beats may be selected as a true heart beat while the others are rejected. In some embodiments, the heart beats that are ultimately selected as true do not have overlapping neighborhood widths. In some embodiments, the value of the assigned neighborhood widths may be empirically determined.

In some embodiments, a likelihood score may be calculated for each candidate heart beat using one or more features (or parameters) of each of the candidate heart beats, such as the shape and morphology of the candidate heart beat, the amplitude of the candidate heart beat, the noise associated with the candidate heart beat, etc. In some embodiments, a likelihood score may represent the probability that a candidate heart beat is a true heart beat. In some embodiments, values of the various features or parameters may be combined in various mathematical and/or logical ways to determine an overall likelihood score for a candidate heart beat.

In some embodiments, individualized neighborhood widths may be computed for each of the candidate heart beats according to the computed likelihood score of each candidate. In some embodiments, an inverse relationship may exist between the likelihood score and the neighborhood width (in the time domain) assigned to each of the candidate R-wave. Generally, the larger the likelihood score, the smaller the chosen neighborhood width of a candidate heart beat.

In some embodiments, scaling may be applied to the neighborhood widths of the heart beats according to one or more previous heart rate statistics. Generally, a lower previous heart rate (with true heart beats that are further apart in time) may dictate larger neighborhood widths as fewer true heart beats are expected to be present within a given time window; on the other hand, a higher previous heart rate (with true heart beats that are closer together in time) may dictate smaller neighborhood widths as more true heart beats are expected to be present within a given time window.

Accordingly, in some embodiments, when the scaling factor is applied, in response to a generally lower previous heart rate based on previous heart rate statistics, a scaling factor value may be chosen such that the time neighborhood widths become larger, thereby causing a smaller number heart beats to be chosen as true heart beats within a given time window; on the other hand, in response to a generally higher previous heart rate, a scaling factor value may be chosen such that the time neighborhood widths become smaller, thereby causing a greater number of heart beats to be chosen as true heart beats within a given time window.

In some embodiments, the most recent heart rate data detected of a subject may be used as a part of the previous heart rate statistics. For example, a weighted average/summation of historical heart rate values of a subject may be used as part of the previous heart rate statistics. In some embodiments, a decreasing exponential weighting strategy may be used to obtain the weighting factor values to be used in the computation of the weighted average.

In some embodiments, the shape and form of a candidate R-wave may be used as one of the features in determining the likelihood score. True R-waves are typically characterized by sharp drops (or rises) on both sides of the detected wave. Thus, R-waves may be examined to determine whether a candidate R-wave drops (or rises) sharply enough on both sides of the peak (valley) of the R-wave. Accordingly, a candidate R-wave that does not meet this requirement (i.e., the drop or rise on one side is not sharp enough; or has a drop on one side and a rise on the other) may cause a very low likelihood score to be assigned. On the other hand, a candidate R-wave that does have sharp enough drops (or rises) on both sides of the peak (valley) may cause a regular or high likelihood score to be assigned.

In some embodiments, the detected heart beat information is used in a system designed to detect seizures in a patient. For example, such a system could be used on a patient suffering from epilepsy by detecting heart beat information, which is then used in a cardiac-based seizure detection system to detect and/or log seizures. The detected heart beat information could be used in a seizure detection system relying on, for example, cardiac data alone, cardiac data with patient motion data (e.g., accelerometer), or cardiac data with neurological data (e.g., electroencephalogram "EEG") to detect seizures.

Figure 2:
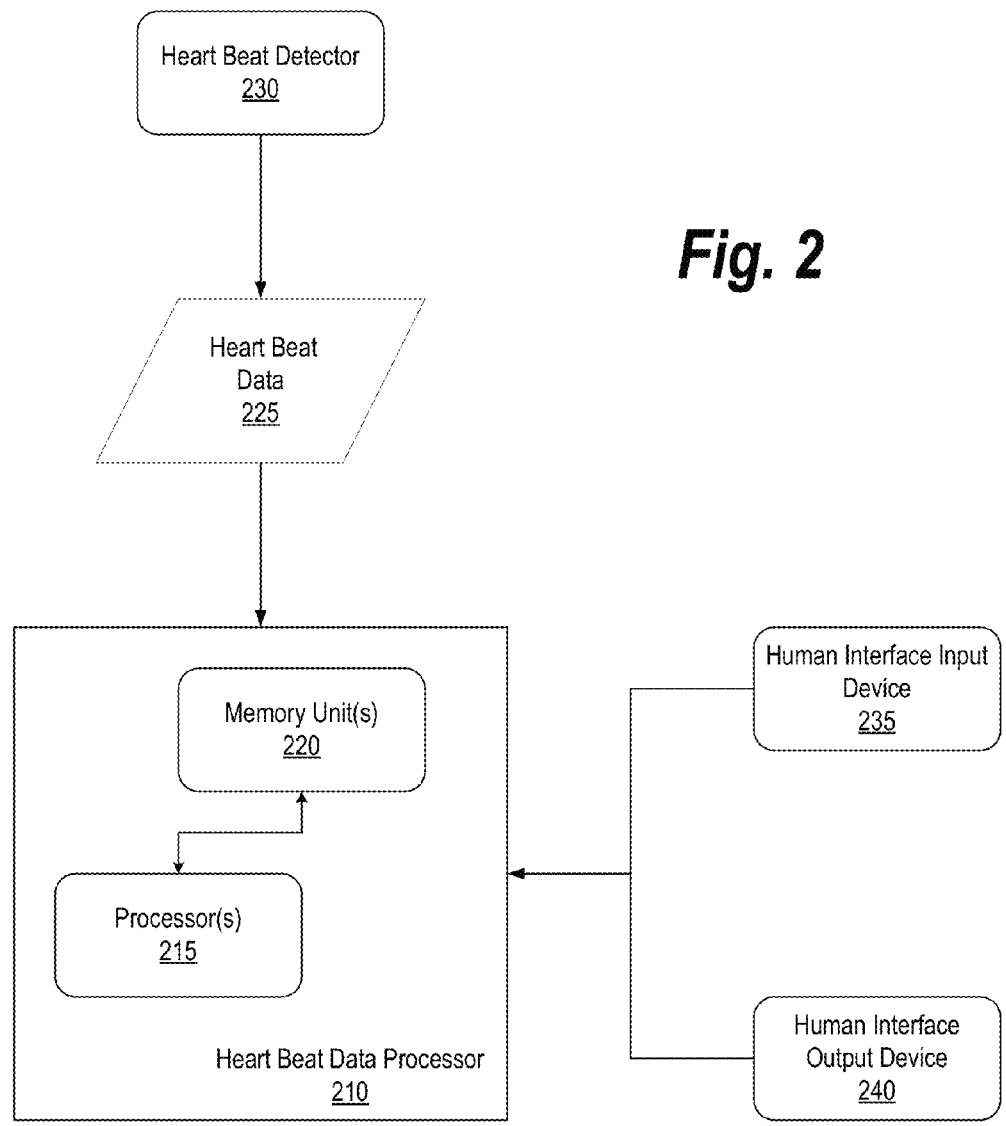
FIG. 2 is a block diagram illustrating an alternative system for adjusting neighborhood widths of candidate heart beats according to a previous heart rate statistics, in accordance with some embodiments.

FIG. 2 is a block diagram illustrating an alternative system for adjusting neighborhood widths of candidate heart beats according to a previous heart rate statistics, in accordance with some embodiments.

In some embodiments, heart beat data processor 210 is configured to receive and analyze heart beat data 225 as described here. Heart beat data 225 may be raw ECG recordings or filtered or preprocessed ECG recordings at given points in time (generally in a given time window). The heart beat data may be received in real time or near real time from heart beat detector 230, which may comprise electrocardiogram (ECG) equipment and preprocessing modules configured to record, filter and preprocess raw ECG of a subject, and divide the continuous ECG into a sequence of overlapping or non-overlapping time windows of ECG. Or the heart beat data may be previously recorded and is being received from a storage device.

Heart beat data processor 210 may be configured, in some embodiments, to preprocess ECG data, to calculate multiple features, to generate candidate heart beats, to calculate a corresponding likelihood score for each candidate, and to apply a scaling to the neighborhood widths of candidate R-waves within a time window according to previous heart rate statistics of a subject.

Heart rate data analyzer 210 may also be coupled to human interface input device 235 and human interface output device 240. Human interface input device 235 may be configured to provide a user of the system a means with which to input data into the system and with which to generally control various options. Accordingly, human interface input device 235 may be at least one of a computer keyboard, a touch screen, a microphone, a video camera, etc.

Human interface output device 240 may be configured to provide information to a user of the system visually, audibly, etc. Accordingly, human interface output device 240 may be at least one of a computer display, one or more audio speakers, haptic feedback devices, etc.

Figure 3:
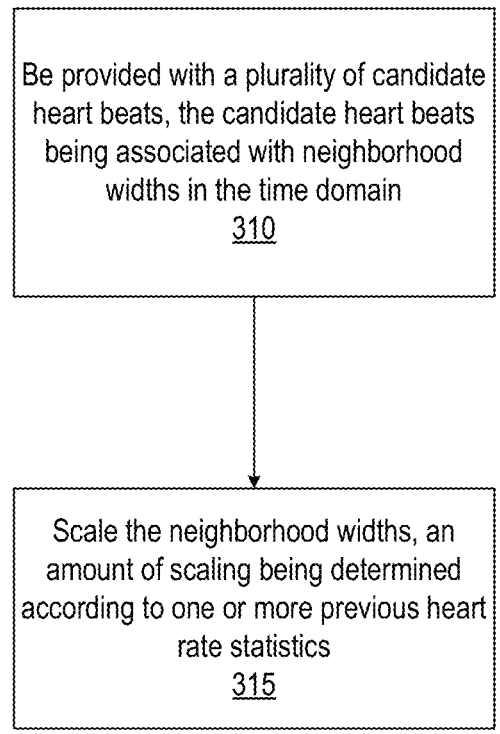
FIG. 3 is a flow diagram illustrating a method for adjusting neighborhood widths of candidate heart beats according to a previous heart rate statistics, in accordance with some embodiments.

FIG. 3 is a flow diagram illustrating a method for adjusting neighborhood widths of candidate heart beats according to a previous heart rate statistics, in accordance with some embodiments.

In some embodiments, the method illustrated in this figure may be performed by one or more of the systems illustrated in FIG. 1 and FIG. 2.

At block 310, a plurality of candidate heart beats are provided, the candidate heart beats being associated with neighborhood widths in the time domain.

At block 315, the neighborhood widths are scaled, an amount of scaling being determined according to one or more previous heart rate statistics.

Figure 4:
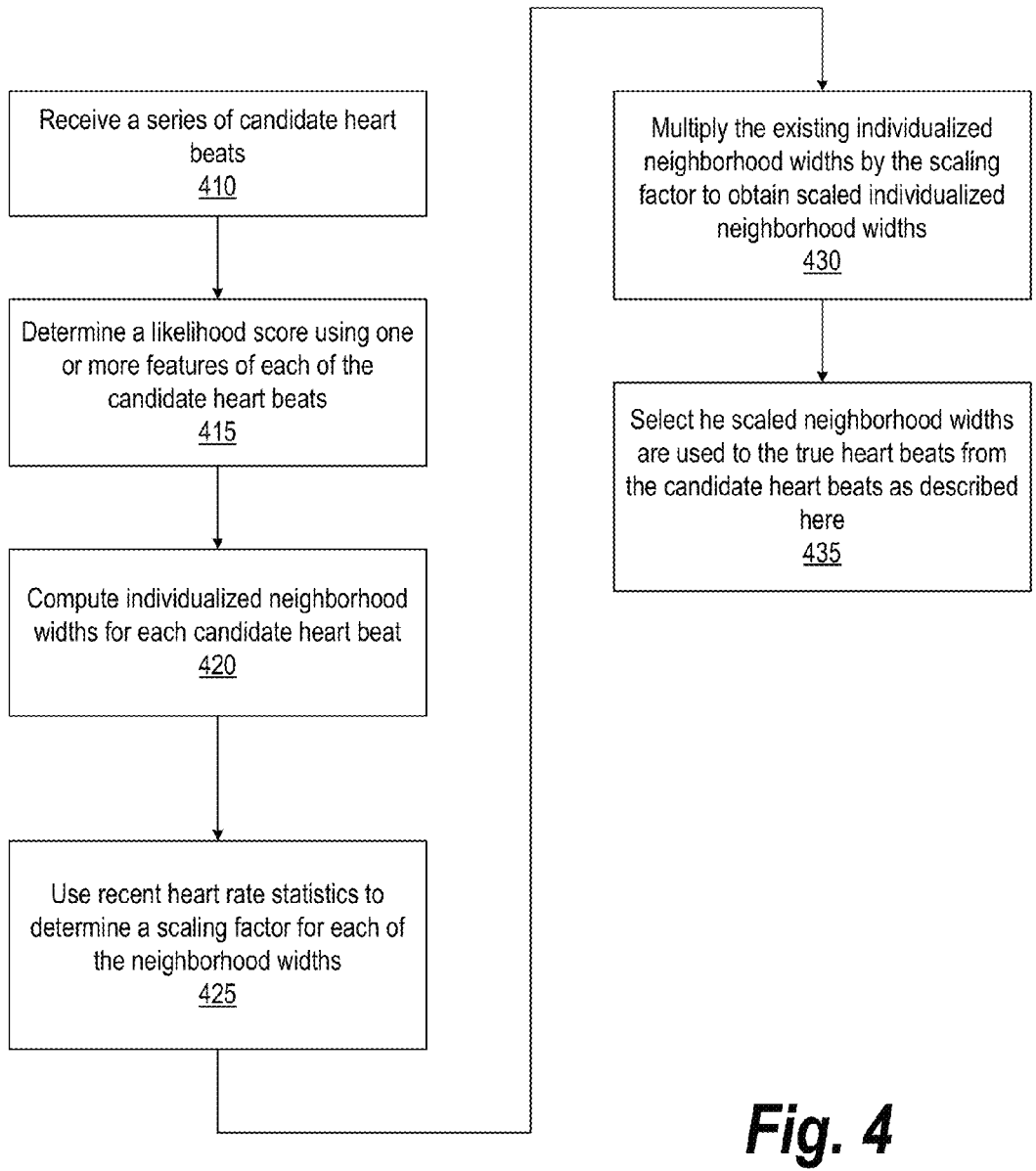
FIG. 4 is a flow diagram illustrating an alternative method for adjusting neighborhood widths of candidate heart beats according to a previous heart rate statistics, in accordance with some embodiments.

FIG. 4 is a flow diagram illustrating an alternative method for adjusting neighborhood widths of candidate heart beats according to a previous heart rate statistics, in accordance with some embodiments.

In some embodiments, the method illustrated in this figure may be performed by one or more of the systems illustrated in FIG. 1 and FIG. 2.

At block 410, a series of candidate R-waves are received. In some embodiments, electrocardiogram (ECG) may be used to detect the R-wave portion of heart beats.

At block 415, as described here, a likelihood score may be determined using one or more features of each of the candidate heart beats. In some embodiments, the likelihood score may represent the probability that a candidate heart beat is a true heart beat.

At block 420, individualized neighborhood widths for each candidate heart beat are computed. In some embodiments, the neighborhood widths may be computed using the likelihood score of each candidate heart beat. In some embodiments, the neighborhood widths and the likelihood score value exhibit an inverse relationship.

At block 425, recent heart rate statistics are used to determine a scaling factor value for the neighborhood widths within a time window. In some embodiments, the scaling factor value has an inverse relationship to the previous heart rate calculated based on recent heart rate statistics.

At block 430, the existing individualized neighborhood widths are multiplied by the scaling factor to obtain scaled individualized neighborhood widths.

At block 435, the scaled neighborhood widths are used to select the true heart beats from the candidate heart beats within a time window as described here.

Figure 5:
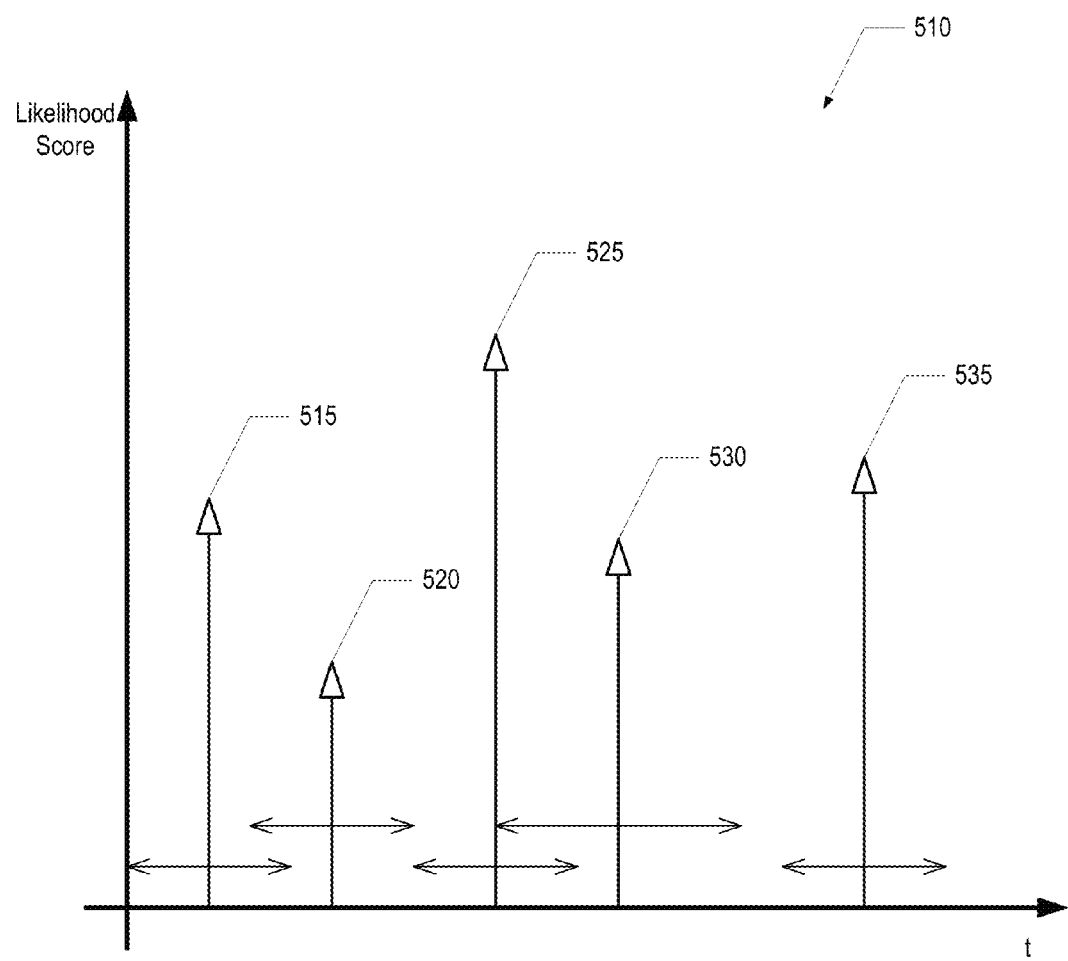
FIG. 5 is a graph illustrating candidate heart beats (R-waves) each having a time neighborhood width, in accordance with some embodiments.

FIG. 5 is a graph illustrating candidate heart beats (R-waves) each having a time neighborhood width, in accordance with some embodiments.

Graph 510 shows five example candidate R-waves representation, with each candidate R-wave having a time neighborhood width, indicated by the widths centered about each R-wave, and an individualized likelihood score, indicated by the height of the arrow of each candidate R-wave. The time neighborhood width of a candidate R-wave may be determined partly by, and be inversely related to, the value of the likelihood score of the candidate R-wave as described here. The neighborhood width may also be scaled using previous heart rate statistics as described here.

In some embodiments, a candidate R-wave may be identified as a false R-wave, in response to determining that: the time neighborhood width of another candidate R-wave, which has a higher likelihood score value, overlaps with the time neighborhood width of this candidate R-wave.

Applying the above condition to the example shown, candidate R-wave 535 is selected as a true R-wave since its time neighborhood width does not overlap with that of any other candidate R-wave. Candidate R-wave 525 is also selected as true, because its time neighborhood width only overlaps with that of 530, and its individualized likelihood score value is higher. Accordingly, candidate R-wave 530 is identified as false and is rejected. Similarly, candidate R-wave 515 is selected as true and the candidate R-wave 520 is identified as false and is rejected as the time neighborhood width of candidate R-wave 520 overlaps with that of candidate R-wave 515 and 515 has a higher value of the likelihood score.

Figure 6:
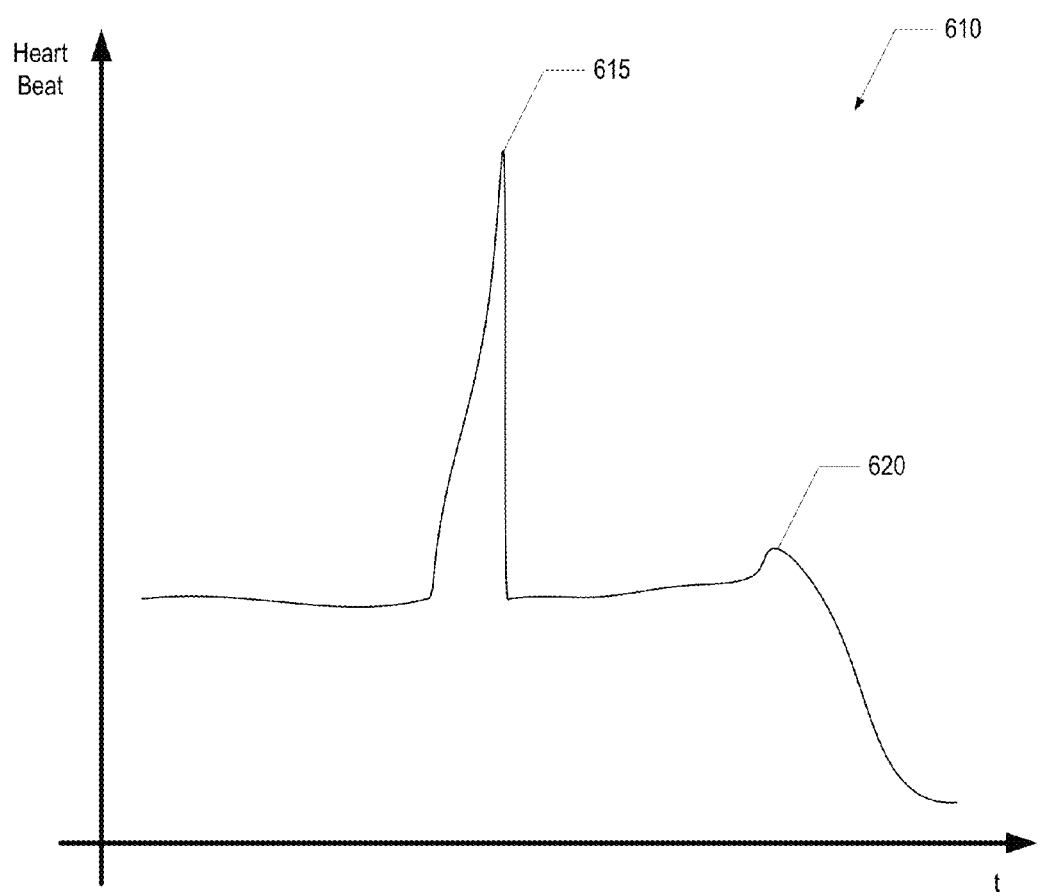
FIG. 6 is a graph illustrating two candidate heart beats (R-waves) of different shapes and waveforms, in accordance with some embodiments.

FIG. 6 is a graph illustrating two candidate heart beats (R-waves) of different shapes and waveforms, in accordance with some embodiments.

Graph 610 shows two examples of candidate R-waves: the candidate R-wave 615 and the candidate R-wave 620. In some embodiments, the shape of a candidate R-wave may be considered as one of the factors or features in determining the value of the likelihood score of the candidate R-wave.

In some embodiments, the sharpness of a candidate R-wave may be measured by examining the slope on both sides of the R-wave peak (or valley). A true R-wave typically has very sharp drops (or rises) on both sides of the R-wave peak (or valley). Therefore, candidate R-wave 615 meets the requirement on the sharpness of true R-waves as it exhibits sharp drops on both sides of R-wave peak, which may result in a normal or large value in the likelihood score of the candidate R-wave.

On the other hand, candidate R-wave 620 does not meet the sharpness requirement as it exhibits a sharp drop on one side and a flat drop on the other side of the R-wave peak. Accordingly, a very low the likelihood score value may be assigned to candidate R-wave 620.

In some embodiments, a mathematical function may be designed to measure the sharpness of a candidate R-wave, which may, for example, consider the slopes of a candidate R-wave on both sides of the peak (valley), and according to the slopes on both sides assign a sharpness score, as a sub score of the sharpness feature, to the candidate R-wave. The sharpness score may then be combined with other sub scores determined by other features, to determine an overall likelihood score.

Figure 7:
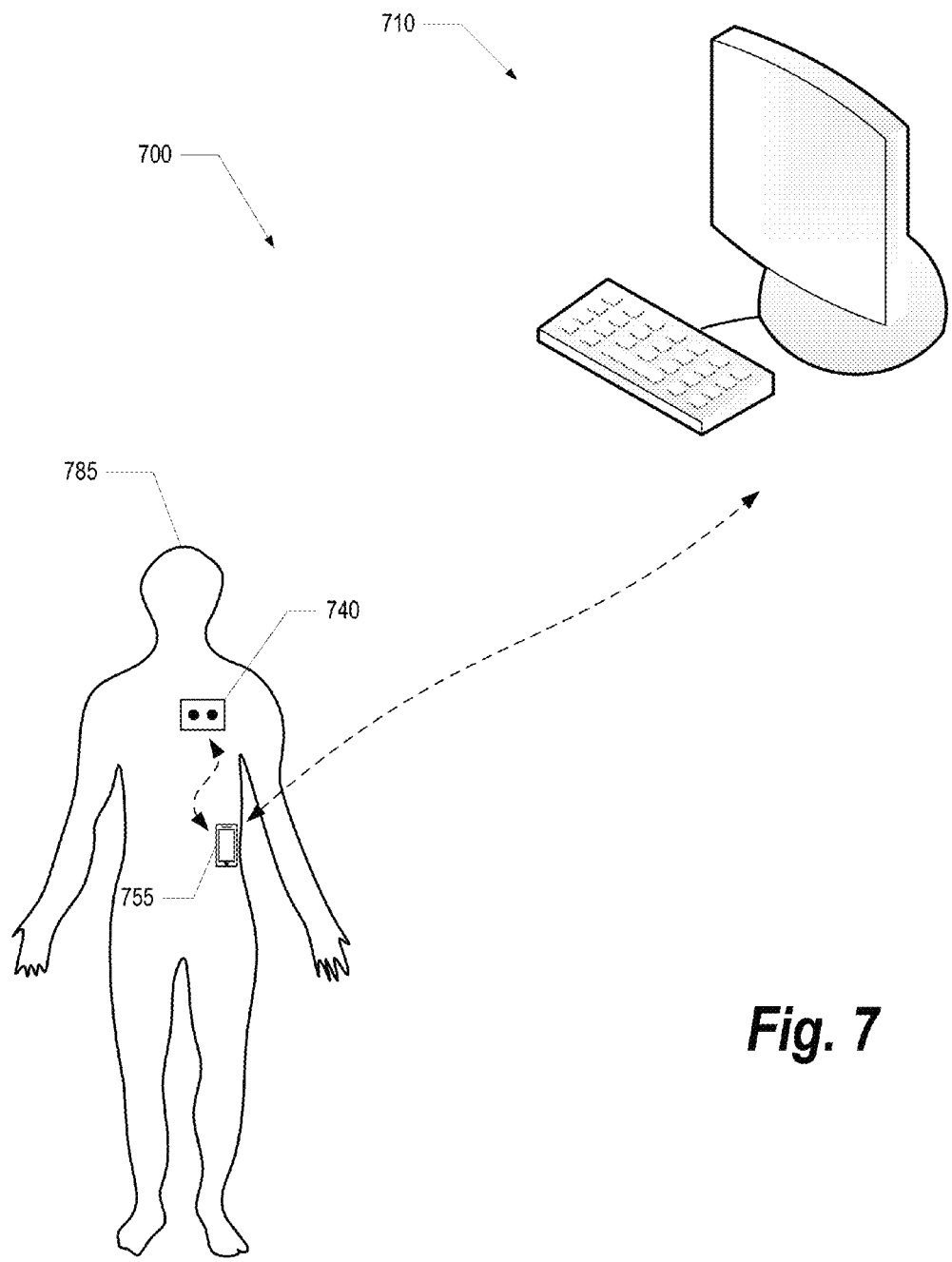
FIG. 7 is a diagram illustrating an example of the application of an electrocardiogram to a subject, in accordance with some embodiments.

FIG. 7 is a diagram illustrating an example of the application of an electrocardiogram to a subject, in accordance with some embodiments.

A particular embodiment of a system for monitoring heart beat data from a subject is shown in the Figure and generally designated 700. System 700 may include, a heart beat sensor 740, a controller 755, and a computer 710.

In some embodiments, heart beat and/or heart rate data may be collected by using an external or implanted heart beat sensor and related electronics (such as heart beat sensor 740), and a controller that may be wirelessly (or via wire) coupled to the sensor, such as controller 755. In one embodiment, sensor 740 may comprise electrodes in an externally worn patch adhesively applied to a skin surface of patient 785. In some embodiments, sensor 740 may be implanted under the patient's skin. The patch may include electronics for sensing and determining a heart beat signal (e.g., an ECG signal), such as an electrode, an amplifier and associated filters for processing the raw heart beat signal, an A/D converter, a digital signal processor, and in some embodiments, an RF transceiver wirelessly coupled to a separate controller unit, such as controller 755. In some embodiments, the controller unit may be part of the patch electronics.

The controller 755 may comprise electronics and memory for performing computations. In some embodiments, the controller 755 may include a display and an input/output device. The controller 755 may comprise part of a handheld computer such as a PDA or smartphone, a cellphone, an iPod® or iPad®, etc.

In the example shown, sensor 740 may be placed on a body surface suitable for detection of heart signals. Electrical signals from the sensing electrodes may be then fed into patch electronics for filtering, amplification and A/D conversion and other preprocessing, and creation of a time-of-beat sequence (e.g., an R-R interval data stream), which may then be transmitted to controller 755. Sensor 740 may be configured to perform various types of processing to the heart rate data, including filtering, determination of R-wave peaks, calculation of R-R intervals, etc. In some embodiments, the patch electronics may include the functions of controller 755, illustrated in FIG. 7 as separate from sensor 740.

The time-of-beat sequence may be then provided to controller 755 for processing and determination of various metrics. Controller 755 may be configured to communicate with computer 710. Computer 710 may be located in the same location or computer 710 may be located in a remote location from controller 755. Computer 710 may be configured to further analyze the heart data, store the data, retransmit the data, etc. Computer 710 may comprise a display for displaying information and results to one or more users as well as an input device from which input may be received by the one or more users.

Figure 8:
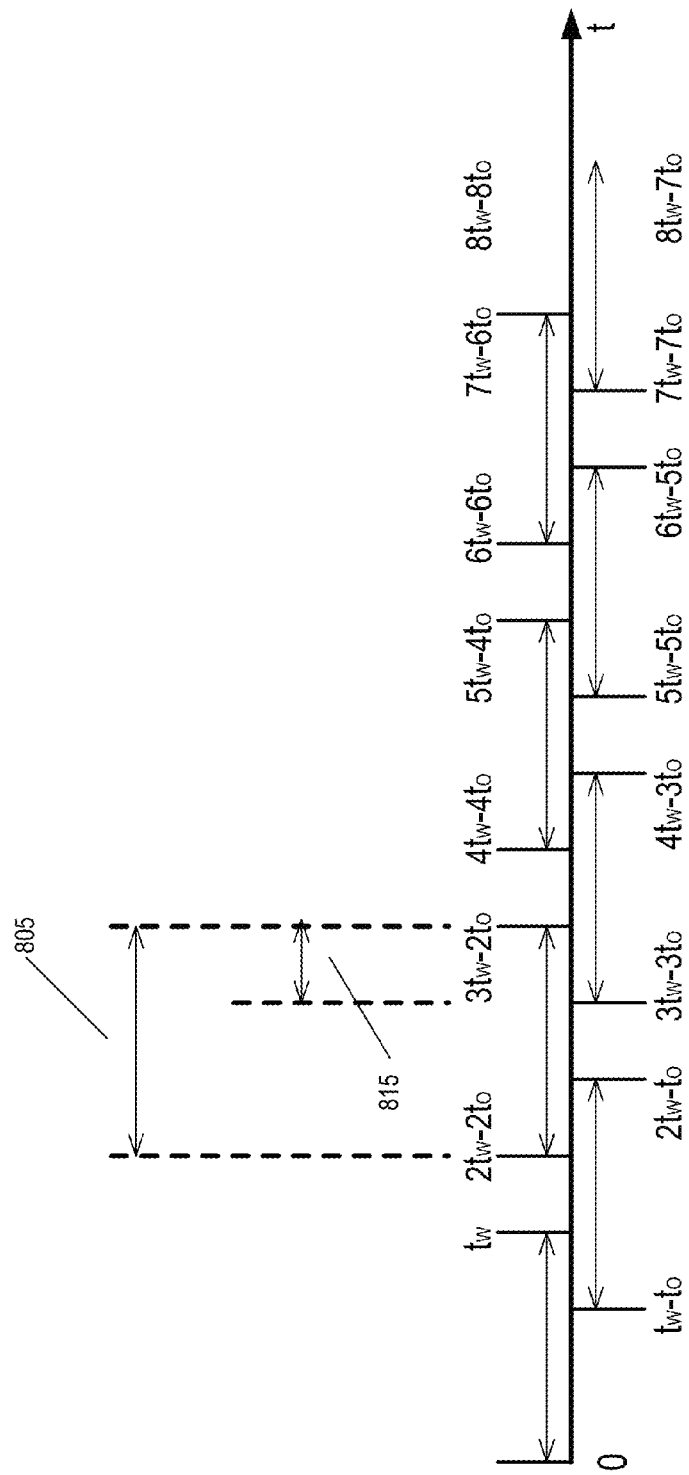
FIG. 8 is a graphical diagram illustrating the time windows strategy used in processing the heart beat data, in accordance with some embodiments.

FIG. 8 is a graphical diagram illustrating the time windows strategy used in processing the heart beat data, in accordance with some embodiments.

The figure shows an example of how a continuous time of ECG recording may be divided into time windows, of ECG segments (epochs) as processing units, for the purpose of detecting true heart beats from the preprocessed ECG recording within those time intervals. In some embodiments, without loss of generality, intervals may be chosen to have a width of $t_w$ in time—as is the case, for example, for interval 805. In addition, without loss of generality, the time intervals may be chosen to have an overlap of $t_o$—as is the case, for example, for interval 815. The same pattern may be repeated for continuing processing of the ECG recordings and/or other input data. In addition, the 'previous time period', which may be used for calculating the previous heart rate statistics, is updated at the beginning of processing a new time window of ECG segment.

FIG. 9 is a graphical diagram illustrating an example of previous heart rate statistics where exponentially decreasing weights are used with the previous heart rate data, in accordance with some embodiments.

FIG. 9 depicts one example of how recent heart rate statistics may be computed for processing and detecting true heart beats in the current time window 910. Current time window 910 may be the interval where features are being computed from the ECG segment in order to detect true heart beats (R-waves). The features being computed may include without limitation, for example, generating candidate heart beats, calculating the likelihood score, calculating the dynamical scaling factor, calculating the neighborhood width, screening candidate heart beats, and selecting candidate heart beats. In some embodiments, as described here, previous heart rate statistics may be used for dynamically adjusting the neighborhood widths of candidate heart beats within a time window by multiplying the neighborhood widths by a scaling factor in the screening and selection process for true heart beats.

In some embodiments, a previous weighted average heart rate may be computed from the detected heart rate data prior to the current time window 910 using a decreasing exponential weighting average strategy based on previous local average heart rates. The result of a previous weighted average heart rate may be used to dynamically adjust the neighborhood widths by multiplying the neighborhood widths with a scaling factor. As is shown in the example, first, the previous heart rate time period may be divided into 60 s intervals, and a local average heart rate may be computed for each of those 60 s intervals. Then, in order to compute the overall average, each 60 s local average heart rate may be weighted according to the value of the decreasing exponential function at the center of that subinterval. Thus, more recent heart rate values are given higher weights compared to the heart rate values from further into the past. The weights may be non-negative and may be normalized.

In some embodiments, a previous weighted average heart rate may be computed from the detected heart rate data prior to the current time window 910 using a weighting average strategy that decreases linearly based on previous local average heart rates. In some embodiments the weighting average strategy decreases non-linearly. In some embodiments the weighting average strategy decreases at varying rates depending on heart rate statistics, neurological statistics, autonomic statistics, or similar computed or detected features. In some embodiments the weighting average strategy decreases at varying rates depending on input from the patient or other user.

It should be noted that various other methods may be used to calculate previous heart rate based on the previous heart rate data or statistics, for the purpose of dynamically adjusting the neighborhood widths within a time window in the selection of true heart beats.

The previous description of the disclosed embodiments is provided to enable any person skilled in the art to make or use the present claimed subject matter. Various modifications to these embodiments will be readily apparent to those skilled in the art, and the generic principles defined herein may be applied to other embodiments without departing from the spirit or scope of the claimed subject matter. Thus, the present claimed subject matter is not intended to be limited to the embodiments shown herein but is to be accorded the widest scope consistent with the principles and novel features disclosed here.

The benefits and advantages that may be provided by the present claimed subject matter have been described above with regard to specific embodiments. These benefits and advantages, and any elements or limitations that may cause them to occur or to become more pronounced are not to be construed as critical, required, or essential features of any or all of the claims. As used here, the terms "comprises," "comprising," or any other variations thereof, are intended to be interpreted as non-exclusively including the elements or limitations which follow those terms. Accordingly, a system, method, or other embodiment that comprises a set of elements is not limited to only those elements and may include other elements not expressly listed or inherent to the claimed embodiment.

While the present claimed subject matter has been described with reference to particular embodiments, it should be understood that the embodiments are illustrative and that the scope of the claimed subject matter is not limited to these embodiments. Many variations, modifications, additions and improvements to the embodiments described above are possible. It is contemplated that these variations, modifications, additions and improvements fall within the scope of the present disclosure as detailed within the following claims.

What is claimed is:

1. A method comprising:
   selecting, via a data processor, candidate heart beats during a time interval from heart beat data of a patient;
   assigning, via the data processor, a likelihood score to each candidate heart beat of the candidate heart beats, wherein the likelihood score assigned to each candidate heart beat indicates a probability that the candidate heart beat is a true heart beat;
   assigning, via the data processor, an extent in a time domain for each candidate heart beat, wherein the extent in the time domain for a particular candidate heart beat has an inverse relationship to the likelihood score assigned to the particular candidate heart beat; and
   identifying, via the data processor, true heart beats from the candidate heart beats based at least in part on the likelihood score and the extent in the time domain assigned to each candidate heart beat.

2. The method of claim 1, further comprising:
   determining, via the data processor, a scaling factor for the time interval based on previous heart rate data; and
   adjusting each extent in the time domain by the scaling factor prior to identifying true heart beats from the candidate heart beats.

3. The method of claim 2, wherein the scaling factor is larger than one when a statistic generated from the previous heart rate data is below a particular value.

4. The method of claim 2, wherein the scaling factor is less than one when a statistic generated from the previous heart rate data is above a particular value.

5. The method of claim 1, wherein assigning the likelihood score to a particular candidate heart beat comprises:
   analyzing a sharpness of signal strength of the particular candidate heart beat as a function of time from the heart beat data; and
   choosing a value for the likelihood score of the particular candidate based at least in part on the sharpness.

6. The method of claim 1, wherein identifying true heart beats comprises:
   determining that a first extent in the time domain associated with a first candidate heart beat overlaps at least a portion of a second extent in the time domain associated with a second candidate heart beat; and
   eliminating the first candidate heart beat from consideration as a true heart beat when a first likelihood score for the first candidate heart beat is less than a second likelihood score for the second candidate heart beat.

7. The method of claim 1, further comprising detecting occurrence of a seizure based on identified true heart beats.

8. A system comprising:
   one or more processors;
   one or more memory units coupled to the one or more processors, wherein the one or more memory units include instructions executable by the one or more processors to:
      determine candidate heart beats during a time interval from heart beat data of a patient;
      assign a likelihood score and an extent in a time domain to each candidate heart beat, wherein the likelihood score indicates a probability that the candidate heart beat is a true heart beat;
      determine a scaling factor for the time interval based on previous heart beat data;
      scale each extent in the time domain with the scaling factor to generate a scaled extent in the time domain for each candidate heart beat; and
      identify true heart beats from the candidate heart beats based at least in part on the likelihood scores and the scaled extents in the time domain.

9. The system of claim 8, further comprising a storage device coupled to the one or more processors, wherein the heart beat data is received by the one or more processors from the storage device.

10. The system of claim 8, further comprising a heart beat detector coupled to the one or more processors, wherein the heart beat detector sends the heart beat data of the patient to the one or more processors.

11. The system of claim 10, where the heart beat detector comprises electrocardiogram equipment.

12. The system of claim 8, wherein the one or more memory units include instructions executable by the one or more processors to:
   analyze a sharpness of a particular candidate heart beat; and
   determine the likelihood score of the particular candidate heart beat according to the sharpness of the particular candidate heart beat.

13. The system of claim 8, where the likelihood score for a particular candidate heart beat is determined based on one or more of a shape and morphology of the particular candidate heart beat, an amplitude of the particular candidate heart beat, and noise associated with the particular candidate heart beat.

14. The system of claim 8, wherein the one or more memory units include instructions executable by the one or more processors to detect an occurrence of a seizure based on candidate heart beats identified as true heart beats.

15. A non-transitory computer-readable medium comprising instructions executable by a processor to:
   receive heart beat data of a patient;
   select candidate heart beats during a time interval;
   assign a likelihood score to each candidate heart beat of the candidate heart beats based on at least one feature of each candidate heart beat, wherein the likelihood score indicates a probability that the candidate heart beat is a true heart beat;
   assign an extent in a time domain for each candidate heart beat of the candidate heart beats, wherein the extent in the time domain assigned to a candidate heart beat has an inverse relationship to the likelihood score assigned to the candidate heart beat; and identify true heart beats from the candidate heart beats based at least in part on the likelihood scores and the extents in the time domain.

16. The non-transitory computer-readable medium of claim 15, wherein the heart beat data is received from electrocardiogram equipment.

17. The non-transitory computer-readable medium of claim 15, wherein the instructions further comprise instructions executable by the processor to adjust each extent in the time domain by a scaling factor for the time interval prior to identification of true heart beats from the candidate heart beats, wherein the scaling factor is determined based on previous heart beat data for the patient.

18. The non-transitory computer-readable medium of claim 17, wherein the previous heart beat data for the patient is used to determine a weighted average heart beat rate, and wherein the weighted average heart beat rate is used to determine whether the scaling factor increases the extents in the time domain.

19. The non-transitory computer-readable medium of claim 18, wherein the weighted average heart beat rate is determined based on a decreasing exponential weighting strategy.

20. The non-transitory computer-readable medium of claim 15, wherein the instructions to identify true heart beats from the candidate heart beats include instructions executable by the processor to identify a particular candidate heart beat as a false heart beat when an extent in the time domain of the particular candidate heart beat overlaps an extent in the time domain of another candidate heart beat that has a higher likelihood score.

21. The non-transitory computer-readable medium of claim 15, wherein the instructions to identify true heart beats from the candidate heart beats include instructions executable by the processor to:
  determine whether a particular extent in the time domain associated with a candidate heart beat is overlapped by one or more other extents in the time domain associated with other candidate heart beats; and
  identify the candidate heart beat corresponding to the particular extent in the time domain as a true heart beat when the particular extent in the time domain is not overlapped by the one or more other extents in the time domain associated with the other candidate heart beats.

* * * * *